United States Patent [19]

Convents et al.

[11] Patent Number: 5,443,750
[45] Date of Patent: Aug. 22, 1995

[54] DETERGENT COMPOSITIONS WITH HIGH ACTIVITY CELLULASE AND SOFTENING CLAYS

[75] Inventors: André Convents, Diegem; Alfred Busch, Londerzeel; André C. Baeck, Bonheiden, all of Germany

[73] Assignee: The Procter & Gamble Company, Cincinnati, Ohio

[21] Appl. No.: 90,013

[22] PCT Filed: Jan. 13, 1992

[86] PCT No.: PCT/US92/00190

§ 371 Date: Jul. 15, 1993

§ 102(e) Date: Jul. 15, 1993

[87] PCT Pub. No.: WO92/13053

PCT Pub. Date: Aug. 6, 1992

[30] Foreign Application Priority Data

Jan. 16, 1991 [EP] European Pat. Off. ............ 91870006
Nov. 6, 1991 [EP] European Pat. Off. ............ 91202880

[51] Int. Cl.$^6$ .................. C11D 3/386; C12N 9/42; C12N 15/56; C12N 15/80
[52] U.S. Cl. ................... 252/174.12; 435/209; 435/691; 435/252.3; 435/265; 536/23.2; 935/14; 935/68
[58] Field of Search ............... 435/183, 200, 209, 69.1, 435/252.33, 320.1; 566/23.2; 252/174.12, 180; 210/696–701

[56] References Cited

U.S. PATENT DOCUMENTS

| | | | |
|---|---|---|---|
| 4,327,189 | 4/1982 | Crutchfield | 501/148 |
| 4,435,397 | 3/1984 | Barbesgaard et al. | 252/174.12 |
| 4,844,821 | 7/1989 | Mermelstein et al. | 252/8.7 |
| 4,943,530 | 7/1990 | Christner et al. | 435/188 |
| 4,978,470 | 12/1990 | Suzuki et al. | 252/174.12 |
| 5,071,587 | 12/1991 | Perman | 252/181 |
| 5,075,227 | 12/1991 | Hagen | 435/172.3 |
| 5,298,405 | 3/1994 | Nevalainen et al. | 435/209 |
| 5,364,553 | 11/1993 | Cao | 252/174.12 |

FOREIGN PATENT DOCUMENTS

| | | |
|---|---|---|
| 0137280 | 4/1985 | European Pat. Off. . |
| 0177165 | 4/1986 | European Pat. Off. . |
| 0269168 | 6/1988 | European Pat. Off. . |
| 0269169 | 6/1988 | European Pat. Off. . |
| 0297673 | 1/1989 | European Pat. Off. . |
| 0350098 | 1/1990 | European Pat. Off. . |
| 0367339 | 5/1990 | European Pat. Off. . |
| 0368589 | 5/1990 | European Pat. Off. . |
| 0381397 | 8/1990 | European Pat. Off. . |
| 0381487 | 8/1990 | European Pat. Off. . |
| 8504672 | 10/1985 | WIPO . |
| WO89/09259 | 1/1989 | WIPO . |
| WO89/04862 | 6/1989 | WIPO . |
| WO89/08695 | 9/1989 | WIPO . |
| WO91/1724S | 11/1991 | WIPO . |

*Primary Examiner*—Robert A. Wax
*Assistant Examiner*—William W. Moore
*Attorney, Agent, or Firm*—Ken K. Patel; Jacobus C. Rasser; Jerry J. Yetter

[57] ABSTRACT

The present invention relates to detergent compositions comprising a high activity cellulase in combination with a softening clay. In the detergent compositions herein, the cellulase comprises a cellulase of high activity defined by the C14CMC-method. Preferably the detergent composition comprises a softening clay together with a clay flocculating agent and in case of liquid composition an anti-settling agent for the clay.

26 Claims, No Drawings

DETERGENT COMPOSITIONS WITH HIGH ACTIVITY CELLULASE AND SOFTENING CLAYS

TECHNICAL FIELD

The present invention relates to detergent compositions comprising a high activity cellulase in combination with a softening clay. In the detergent compositions herein, the cellulase comprises a cellulase of high activity defined by the C14CMC-method. Preferably the detergent composition comprises a softening clay together with a clay flocculating agent and in case of liquid composition an anti-settling agent for the clay.

The present invention relates to detergent compositions comprising a high activity cellulase in combination with a softening clay. In the

BACKGROUND OF THE INVENTION

The need for detergent compositions which exhibit not only good cleaning properties, but also good fabric-softening performance, and other fabric care benefits, is well-established in the art.

The efficiency of cellulolytic enzymes, i.e. cellulases, in terms of textile cleaning and harshness-reducing agent for fabrics has been recognized for some time; GB-A-2,075,028, GB-A-2,095,275 and GB-A-2,094,826, disclose detergent compositions with cellulase for improved cleaning performance; GB-A-1,368,599 discloses the use of cellulase for reducing the harshness of cotton-containing fabrics; U.S. Pat. No. 4,435,307 teaches the use of a cellulolytic enzyme derived from Humicola insolens as well as a fraction thereof, designated ACXI, as a harshness-reducing detergent additive.

EP-A-0 269 168 discloses optimized detergent compositions containing cellulase, which are formulated at a mild alkaline pH range and provide combined fabric cleaning, fabric softening, and fabric care performance.

In WO 89109259 have been disclosed cellulase preparations useful for reducing the harshness of cotton-containing fabrics, comprising an endoglucanase component with a high endoase activity and affinity towards cellulose.

The practical exploitation of cellulases has however, been set back by the fact that cellulase preparations such as those disclosed in the above-mentioned prior art documents, are complex mixtures, of which only a certain fraction is effective in the fabric-care context; it was thus difficult to implement cost effective industrial production of cellulase for the detergent industry; and large quantities of such cellulase preparations would need to be applied, in order to obtain the desired effect on fabrics.

Improvements in cellulase production also often have not proven to be sufficiently identifiable in terms of applicability in detergents. Defining a cellulase selection criterium relevant for detergent application of cellulase was made possible by the C14CMC-method disclosed in EP-A-350 098. A minimum of 10% removal of immobilized radioactive labelled carboxymethyl-cellulose has now been found to provide high activity cellulase. A preferred group of cellulase falling under the high activity definition according to the present invention has been disclosed in copending Danish Patent Application No.: 1159/90 filed May 5, 1990. There is amongst others disclosed a cellulase preparation consisting essentially of a homogeneous endoglucanase component which is immunoreactive with a monoclonal antibody raised against a partially purified about 43 kD cellulase derived from Humicola insolens DM1800.

The finding that this particular endoglucanase component of cellulase is advantageous for the treatment of cellulose-containing materials now permits to produce the cellulase cost-effectively, e.g. by employing recombinant DNA techniques, and allows to apply only a small quantity of the cellulase preparation, and obtain the desired effect on fabrics.

EP-A-381 397 discloses the effect of low ionic-strength on enzyme performance, in particular for lipase. However, it has been surprisingly found, that the effect of a compact matrix on the selected enzymes of the present invention is much larger than what could be expected from state of the art cellulases such as disclosed in EP-A-381 397.

In EP-A-177 165 the use of softening clay together with cellulase in detergent compositions has been disclosed. The invention of this disclosure is based on the lack of prior art disclosing the combination of two principal softening or hashness reducing detergent compounds. EP-A-177 165 recognizes that there is no reason to exclude clay or cellulase from detergent compositions comprising the respective other compound. However, EP-A-177 165 does not recognize that for the selected group of highly active cellulase according to the present invention, the combination with clay is advantageous beyond the additive performance which otherwise could be expected of two softening ingredients.

Accordingly, it is an objective of the present invention to provide detergent compositions comprising a high activity cellulase and softening clay, which detergent compositions exhibit an optimum softening performance. An additional objective is to provide such detergent compositions in liquid or granulate form.

It is another objective of the present invention to provide detergent compositions containing high activity cellulase together with softening clay which provide excellent colour rejuvenation and whiteness maintenance for fabrics especially for those which comprise cellulose fibres. An additional objective of the present invention is to provide detergent compositions which further exhibit good stain removal and cleaning performance particularly at temperatures of about 60° C. or below.

It is a further object of the present invention to provide such detergent compositions in a compact form, having a relatively high density and containing a low amount of inorganic filler salt, which exhibit optimum softening performance.

It is yet another objective of the present invention to provide liquid detergent compositions comprising, in addition to the essential compounds of the present invention, an anti-settling agent to provide a storage stable clay suspension matrix. An even further objective of the present invention is to provide detergent compositions, be it liquid or granular comprising in addition to the essential compounds a clay flocculating agent to additionally aid the softening clay deposition on fibres.

SUMMARY OF THE INVENTION

The present invention relates to detergent compositions containing a surface active agent, a builder system and a cellulase wherein said cellulase is characterized by providing at least 10% removal of immobilized, radio-active labelled carboxymethylcellulose according to the C14CMC-method, which is described in detail below, and further characterized in that said detergent composition also comprises a softening clay.

Further preferred are such detergent compositions in which the cellulase consists essentially of a homogeneous endoglucanase component which is immuno-reactive with an anti-body raised against a highly purified endoglucanase, being a cellulase of about 43 Kd, derived from *Humicola insolens*, DSM 1800 or a homologous to the about 43 kD cellulase. Additionally, detergent compositions comprising softening clay and cellulase being an endoglucanase enzyme with the aminoacid sequences shown in the listings SEQ ID NO: 2 and SEQ ID NO: 4 have been found to provide the desired synergetic fabric treatment benefits, particularly softening, according to the present invention.

Definitions

Unless stated otherwise, the following definitions will be used hereinafter:

percentages are percent by weight softening refers to a range of fabric treatments other than cleaning; in particular it includes softening, colour rejuvenation and whiteness maintenance, anti-wrinkling, anti-static and ease of ironing treatments.

Detailed Description of the Invention

The present detergent compositions can be in granular or liquid form. The form depends upon the desired application for example as a softening-through-the-wash detergent, at low or high temperatures, in an automatic washing machine or in a semi-automatic hand washing procedure.

The desired form of the detergent will strongly influence the selection and amounts of compounds of surfactant, builder, cellulase, softening clays and especially optional ingredients for the particular composition. For liquid compositions an anti-settling agent for the softening clay is desirable and not contradictive with flocculating agents used to aid clay deposition on fibres for liquid or granular compositions. However, the detailed description of all individual compounds and the examples will enable the man skilled in the art to formulate detergent compositions according to the present invention.

SURFACTANT

A wide range of surfactants can be used in the detergent compositions. A typical listing of anionic, nonionic, ampholytic and zwitterionic classes, and species of these surfactants, is given in U.S. Pat. No. 3,664,961 issued to Norris on May 23, 1972.

Mixtures of anionic surfactants are particularly suitable herein, especially mixtures of sulphonate and sulphate surfactants in a weight ratio of from 5:1 to 1:2, preferably from 3:1 to 2:3, more preferably from 3:1 to 1:1. Preferred sulphonates include alkyl benzene sulphonates having from 9 to 15, especially 11 to 13 carbon atoms in the alkyl radical, and alpha-sulphonated methyl fatty acid esters in which the fatty acid is derived from a $C_{12}$–$C_{18}$ fatty source preferably from a $C_{16}$–$C_{18}$ fatty source. In each instance the cation is an alkali metal, preferably sodium. Preferred sulphate surfactants are alkyl sulphates having from 12 to 18 carbon atoms in the alkyl radical, optionally in admixture with ethoxy sulphates having from 10 to 20, preferably 10 to 16 carbon atoms in the alkyl radical and an average degree of ethoxylation of 1 to 6. Examples of preferred alkyl sulphates herein are tallow alkyl sulphate, coconut alkyl sulphate, and $C_{14}$–$C_{15}$ alkyl sulphates. The cation in each instance is again an alkali metal cation, preferably sodium.

One class of nonionic surfactants useful in the present invention are condensates of ethylene oxide with a hydrophobic moiety to provide a surfactant having an average hydrophilic-lipophilic balance (HLB) in the range from 8 to 17, preferably from 9.5 to 13.5, more preferably from 10 to 12.5. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

Especially preferred nonionic surfactants of this type are the $C_9$–$C_{15}$ primary alcohol ethoxylates containing 3–8 moles of ethylene oxide per mole of alcohol, particularly the $C_{14}$–$C_{15}$ primary alcohols containing 6–8 moles of ethylene oxide per mole of alcohol and the $C_{12}$–$C_{14}$ primary alcohols containing 3–5 moles of ethylene oxide per mole of alcohol.

Another class of nonionic surfactants comprises alkyl polyglucoside compounds of general formula $$RO(C_nH_{2n}O)_tZ_x$$

wherein Z is a moiety derived from glucose; R is a saturated hydrophobic alkyl group that contains from 12 to 18 carbon atoms; t is from 0 to 10 and n is 2 or 3; x is from 1.3 to 4, the compounds including less than 10% unreacted fatty alcohol and less than 50% short chain alkyl polyglucosides. Compounds of this type and their use in detergent are disclosed in EP-B 0 070 077, 0 075 996 and 0 094 118.

Also suitable as nonionic surfactants are poly hydroxy fatty acid amide surfactants of the formula $$R^2-\underset{\underset{O}{\|}}{C}-\underset{\underset{R^1}{|}}{N}-Z,$$

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or alkenyl chain such as coconut alkyl or mixtures thereof, and Z is derived from a reducing sugar such as glucose, fructose, maltose, lactose, in a reductive amination reaction.

A further class of surfactants are the semi-polar surfactants such as amine oxides. Suitable amine oxides are selected from mono $C_8$–$C_{20}$, preferably $C_{10}$–$C_{14}$ N-alkyl or alkenyl amine oxides and propylene-1,3-diamine dioxides wherein the remaining N positions are substituted by methyl, hydroxyethyl or hydroxypropyl groups.

Another class of surfactants are amphoteric surfactants, such as polyamine-based species.

Cationic surfactants can also be used in the detergent compositions herein and suitable quaternary ammonium surfactants are selected from mono $C_8$–$C_{16}$, preferably $C_{10}$–$C_{14}$ N-alkyl or alkenyl ammonium surfactants wherein remaining N positions are substituted by methyl, hydroxyethyl or hydroxypropyl groups.

Mixtures of surfactant types are preferred, more especially anionic-nonionic and also anionic-nonionic-cationic mixtures. Particularly preferred mixtures are described in British Patent No. 2040987 and European Published Application No. 0 087 914. The detergent compositions can comprise from 1%–70% by weight of surfactant, but usually the surfactant is present in the compositions herein an amount of from 1% to 30%, more preferably from 10–25% by weight.

BUILDER

Builder materials will typically be present at from 10% to 60% of the detergent compositions herein. The compositions herein are free or substantially free of phosphate-containing builders (substantially free being herein defined to constitute less than 1% of the total detergent builder system), and the builder system herein consists of water-soluble builders, water-insoluble builders, or mixtures thereof.

Water insoluble builders can be an inorganic ion exchange material, commonly an inorganic hydrated aluminosilicate material, more particularly a hydrated synthetic zeolite such as hydrated Zeolite A, X, B or HS.

Preferred aluminosilicate ion-exchange materials have the unit cell formula $$M_z[(AlO_2)_z(SiO_2)_y]xH_2O$$

wherein M is a calcium-exchange cation, z and y are at least 6; the molar ratio of z to y is from 1.0 to 0.5 and x is at least 5, preferably from 7.5 to 276, more preferably from 10 to 264. The aluminosilicate materials are in hydrated form and are preferably crystalline containing from 10% to 28%, more preferably from 18% to 22% water.

The above aluminosilicate ion exchange materials are further charaterized by a particle size diameter of from 0.1 to 10 micrometers, preferably from 0.2 to 4 micrometers. The term "particle size diameter" herein represents the average particle size diameter of a given ion exchange material as determined by conventional analytical techniques such as, for example, microscopic determination utilizing a scanning electron microscope. The aluminosilicate ion exchange materials are further characterized by their calcium ion exchange capacity, which is at least 200 mg equivalent of $CaCO_3$ water hardness/g of aluminosilicate, calculated on an anhydrous basis, and which generally is in the range of from 300 mg eq./g to 352 mg eq./g. The aluminosilicate ion exchange materials herein are still further characterized by their calcium ion exchange rate which is described in detail in GB-1,429,143.

Aluminosilicate ion exchange materials useful in the practice of this invention are commercially available and can be naturally occurring materials, but are preferably synthetically derived. A method for producing aluminosilicate ion exchange materials is discussed in U.S. Pat. No. 3,985,669. Preferred synthetic crystalline aluminosilicate ion exchange materials useful herein are available under the designation Zeolite A, Zeolite B, Zeolite X, Zeolite HS and mixtures thereof. In an especially preferred embodiment, the crystalline aluminosilicate ion exchange material is Zeolite A and has the formula $$Na_{12}[(AlO_2)_{12}(SiO_2)_{12}]xH_2O$$

wherein x is from 20 to 30, especially 27. Zeolite X of formula $Na_{86}[(AlO_2)_{86}(SiO_2)_{106}]\cdot 10.276H_2O$ is also suitable, as well as Zeolite HS of formula $Na_6[(AlO_2)_6(SiO_2)_6]7.5H_2O)$.

Another suitable water-insoluble, inorganic builder material is layered silicate, e.g. SKS-6 (Hoechst). SKS-6 is a crystalline layered silicate consisting of sodium silicate ($Na_2Si_2O_5$). The high $Ca^{++}/Mg^{++}$ binding capacity is mainly a cation exchange mechanism. In hot water, the material becomes more soluble.

The water-soluble builder can be a monomeric or oligomeric carboxylate chelating agent.

Suitable carboxylates containing one carboxy group include lactic acid, glycollic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetracarboxylates, cyclopentadienide pentacarboxylates, 2,3,4,5-tetrahydrofuran-cis,-cis,cis-tetracarboxylates, 2,5-tetrahydrofuran-cis-dicarboxylates, 2,2,5,5-tetrahydrofuran-tetracarboxylates, 1,2,3,4,5,6-hexane-hexacarboxylates and and carboxymethyl derivatives of polyhydric alcohols such as sorbitol, mannitol and xylitol. Aromatic polycarboxylates include mellitic acid, pyromellitic acid and the phtalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A, and a water-soluble carboxylate chelating agent such as citric acid. Additionally, builder systems further comprizing polycarboxylate polymers have been found beneficial for the builder system but also for aiding in the softening performance of detergent compositions according to the present invention. Polycarboxylate polymers have been disclosed in detail in the prior art for example in EP-A-137 669.

Other builder materials that can form part of the builder system for the purposes of the invention include inorganic materials such as alkali metal carbonates, bicarbonates, silicates, and organic materials such as the organic phosphonates, amino polyalkylene phosphonates and amino polycarboxylates.

CELLULASE

The activity of enzymes and particularly the activity of cellulase enzyme has been defined for various applications by different analytical methods. These methods all attempt to provide a realistic assessment of the expected in use performance or at least a measurement correlating with the in use performance. As has been detailed in European Patent Application EP-A-350098, many of the methods, particularly these frequently used by cellulase manufacturers, are not sufficiently correlated with the in use performance of cellulase in laundry detergent compositions. This is due to the various other usage conditions for which these activity measurement methods have been developed.

The method described in EP-A-350098, has been developed to be and to have a predictive correlation for the ranking of cellulase activity in laundry detergent compositions.

The present invention therefore uses the method disclosed in EP-A-350098 to screen cellulases in order to distinguish cellulases which are useful in the present invention and those which would not provide the objectives of the present invention. The screening method, hereinafter referred to as C14CMC-Method, which has been adopted from the method disclosed in EP-A-350098, can be described as follows:

Principle

The principle of the C14CMC-Method for screening is to measure at a defined cellulase concentration in a wash solution the removal of immobilized carboxy methyl cellulose (CMC) from a cloth substrate. The removal of CMC is measured by radio-active labelling of some of the CMC by using C14 radio-active carbon. Simple counting of the amount of radio-active C14 on the cloth substrate before and after the cellulase treatment allows the evaluation of the cellulase activity.

Sample Preparation

CMC preparation:
The radio-active CMC stock solution is prepared according to Table I. The radio-active CMC can be obtained by methods referred to in EP-A-350098.
Fabric substrates:
The fabric substrates are muslin cotton swatches having a size of 5 cm×5 cm. They are inocculated with 0.35 ml of the radio-active labelled CMC stock solution in their center. The muslin cotton swatches are then airdried.
Immobilization of CMC:
To immobilize the radio-active labelled CMC on the muslin cotton swatches, laundero-meter equipment "Linitest Original Haunau" made by Original Haunau, Germany, is used. A metal jar of the laundero-meter is filled with 400 ml of hard water (4 mmol/liter of $Ca^{++}$ ions). A maximum number of 13 swatches can be used per jar. The jar is then incubated in a heat-up cycle from 20° C. to 60° C. over 40 minutes in the laundero-meter equipment. After incubation the swatches are rinsed under running city water for 1 minute. They are squeezed and allowed to airdry for at least 30 minutes.

According to EP-A-350098 samples of the swatches with immobilized radio-active CMC can also be measured as "blank samples" without washing.

Sample Treatment

Laundry test solution:
The laundry test solution is prepared according to the composition of Table II. It is balanced to pH 7.5. The laundry test solution is the basis to which a cellulase test sample is added. Care should be taken to not dilute the laundry test solution by adding water to a 100% balance prior to having determined the amount of cellulase to be added. The amount of cellulase which is used in this screening test should be added to provide $25 \times 10^{-6}$ weight percent of cellulase protein in the laundry test solution (equivalent to 0.25 milligram/liter at 14.5° C.).
Wash procedure:
The swatches thus inocculated with radio-active labelled CMC are then treated in a laundry simulation process. The laundry process is simulated in the laundero-meter type equipment, "Linitest, Original Haunau", by Original Haunau, Haunau Germany. An individual swatch is put into a 20 $cm^3$ glass vial. The vial is filled with 10 ml of the laundry test solution and then sealed liquid tight. Up to 5 vials are put into each laundero-meter jar. The jar is filled with water as a heat tranfer medium for the laundering simulation. The laundering simulation is conducted as a heat-up cycle from 20° C. to 60° C. over 40 minutes.

After the processing of the samples the vials are submerged in cold water and subsequently each swatch is taken out of its vial, rinsed in a beaker under running soft water, squeezed and allowed to airdry for at least 30 minutes.

Measurement

In order to measure radio-active labelled CMC removal, a scintillation counter, for example, a LKB 1210 Ultrabeta Scintillation Counter, is used. In order to obtain most accurate results, the instruction manual for optimum operation of the particular scintillation counter should be followed. For example, for the LKB 1210 Ultrabeta Scintillation Counter, the following procedure should be followed. The swatch to be measured is put into a plastic vial filled with 12 ml of scintillator liquid (e.g. scintillator 299 from Packard). The swatch is then allowed to stabilize for at least 30 minutes. The vial is then put into the LKB 1210 Ultrabeta Scintillation Counter and the respective radio-activity counts for the swatch is obtained.

In order to measure the amount of CMC removal due only to the cellulase, a measurement of a swatch which has been inocculated at the same time but has been treated in the laundry test solution without cellulase, is necessary. The activity of the cellulase is then expressed as percent of radio-active labelled CMC removal. This percentage is calculated by the following formula:

$$\% \text{ of radio-active CMC removal} = \frac{XO - XC}{XO} \times 100$$

Wherein
XO is the radioactivity scintillation count of a swatch treated with the laundry test solution without cellulase
XC is the radioactivity scintillation count of a swatch treated with the laundry test solution containing the cellulase to be evaluated Statistical considerations, procedure confirmation:

In order to provide statistically sound results, standard statistical analysis should be employed. For the given example, using the LKB 1210 Ultrabeta Scintillation Counter, it has been found that a sample size of 3 swatches for each radioactivity scintillation count can be used.

In order to confirm the procedure by internal cross-checking, measurement and calculation of the "blank sample" according to EP-A-350098 are recommended. This will allow to detect and eliminate errors.

Interpretation of Results

The described screening test does provide a fast, unique and reliable method to identify cellulases which satisfy the activity criteria of the present invention versus cellulases which are not part of the present invention.

It has been found that a removal of 10% or more of the immobilized radioactive labelled CMC according to the above C14CMC-method, indicates that the respective cellulase satisfies the requirements of the invention.

It will be obvious to those skilled in the art that removal percentages above 10% indicate a higher activity for the respective cellulase. It therefore is contemplated that cellulase providing above 25% or preferably above 50% removal of radioactive labelled CMC, at the protein concentration in the laundry test solution according to the C14CMC-method, would provide indication of an even better performance of the cellulase for use in laundry detergents.

It also has been contemplated that usage of higher concentrations of cellulase for C14CMC-method, would provide higher removal percentages. However, there exists no linear proven correlation between cellulase concentration and removal percentage obtained by it.

It also has been contemplated that usage of higher concentrations of cellulase for C14CMC-method, would provide higher removal percentages.

TABLE I

| Radioactive $C_{14}$ labelled CMC stock solution (all percentages by weight of total solution) | |
|---|---|
| Total CMC* (CMC should be detergent grade CMC with a degree of substitution from about 0.47 to about 0.7) | $99.2 \times 10^{-3}\%$ |
| Ethanol | $14985.12 \times 10^{-3}\%$ |
| Deionized water | $84915.68 \times 10^{-3}\%$ |
| Total | 100% |

*Total CMC contains non-radio-active and radio-active CMC to provide a radioactivity which allows sufficiently clear readings on the scintillation counter used. For example, the radio-active CMC can have an activity of 0.7 millicurie/g and be mixed with non-radio-active CMC at a ratio of 1:6.7.

TABLE II

| Laundry test solution (all percentages by weight of total solution) | |
|---|---|
| Linear $C_{12}$ alkyl benzene sulphonic acid | 0.110% |
| Coconut alkyl sulphate (TEA salt) | 0.040% |
| $C_{12-15}$ alcohol ethoxylate (E07) | 0.100% |
| Coconut fatty acid | 0.100% |
| Oleic acid | 0.050% |
| Citric acid | 0.010% |
| Triethanolamine | 0.040% |
| Ethanol | 0.060% |
| Propanediol | 0.015% |
| Sodium hydroxide | 0.030% |
| Sodium formate | 0.010% |
| Protease | 0.006% |

TABLE II-continued

| Laundry test solution (all percentages by weight of total solution) | |
|---|---|
| Water (2.5 mmol/liter $Ca^{++}$), pH adjustment agent (HCL or NaOH solutions) and cellulase | balance to 100% |

According to the present invention, preferred cellulases are those as described in Danish Patent Application 1159/90. For example, a cellulase preparation useful in the compositions of the invention can consist essentially of a homogeneous endoglucanase component, which is immunoreactive with an antibody raised against a highly purified 43 kD cellulase derived from *Humicola insolens*, DSM 1800, or which is homologous to said 43 kD endoglucanase.

It should be stressed that all cellulase enzymes according to the present invention have to meet the criteria of the above mentioned screening test. However, in the Danish Patent Application 1159/90 additional criteria are established allowing to identify preferred cellulase enzymes in combination with the present screening test.

Cellulase preparations particularly useful in the compositions of the invention are those in which in addition to the screening test, the endoglucanase component exhibits a CMC-endoase activity of at least about 50, preferably at least about 60, in particular at least about 90 CMC-endoase units per mg of total protein. In particular, a preferred endoglucanase component exhibits a CMC-endoase activity of at least 100 CMC-endoase units per mg of total protein.

In the present context, the term "CMC-endoase activity" refers to the endoglucanase activity of the endoglucanase component in terms of its ability to degrade cellulose to glucose, cellobiose and triose, as determined by a viscosity decrease of a solution of carboxymethyl cellulose (CMC) after incubation with the cellulase preparation of the invention, as described in detail below.

The CMC-endoase (endoglucanase) activity can be determined from the viscosity decrease of CMC, as follows: A substrate solution is prepared, containing 35 g/l CMC (Hercules 7 LFD) in 0.1M tris buffer at pH 9.0. The enzyme sample to be analyzed is dissolved in the same buffer. 10 ml substrate solution and 0.5 ml enzyme solution are mixed and transferred to a viscosimeter (e.g. Haake VT 181, NV sensor, 181 rpm), thermostated at 40° C. Viscosity readings are taken as soon as possible after mixing and again 30 minutes later. The amount of enzyme that reduces the viscosity to one half under these conditions is defined as 1 unit of CMC-endoase activity, or CEVU/liter.

SDS polyacrylamide gel electrophoresis (SDS-PAGE) and isoelectric focusing with marker proteins in a manner known to persons skilled in the art were used to determine the molecular weight and isolelectric point (pI), respectively, of the endoglucanase component in the cellulase preparation useful in the present context. In this way, the molecular weight of a specific endoglucanase component was determined to be 43 kD. The isoelectric point of this endoglucanase was determined to be about 5.1.

The cellobiohydrolase activity may be defined as the activity towards cellobiose p-nitrophenyl. The activity is determined as $10^{-6}$ mole nitrophenyl released per minute at 37° C. and pH 7.0. The present endoglucanase component was found to have essentially no cellobiohydrolase activity.

The endoglucanase component in the cellulase preparation herein has initially been isolated by extensive purification procedures, i.a. involving reverse phase HPLC purification of a crude *H. insolens* cellulase mixture according to U.S. Pat. No. 4,435,307. This procedure has surprisingly resulted in the isolation of a 43 kD endoglucanase as a single component with unexpectedly favourable properties due to a surprisingly high endoglucanase activity.

Also, in addition to the screening test, the cellulase enzymes useful in the present compositions can further be defined as enzymes exhibiting endoglucanase activity (in the following referred to as an "endoglucanase enzyme"), which enzymes have the amino acid sequence shown in the appended Sequence Listing SEQ ID NO: 2, or a homologue thereof exhibiting endoglucanase activity.

In the present context, the term "homologue" is intended to indicate a polypeptide encoded by DNA which hybridizes to the same probe as the DNA coding for the endoglucanase enzyme with this amino acid sequence under certain specified conditions (such as presoaking in 5×SSC and prehybridizing for 1 h at 40° C. in a solution of 20% formamide, 5×Denhardt's solution, 50 mM sodium phosphate, pH 6.8, and 50 ug of denatured sonicated calf thymus DNA, followed by hybridization in the same solution supplemented with 100 uM ATP for 18 h at 40° C.).

The endoglucanase enzyme herein may be one produced by species of Humicola such as *Humicola insolens* e.g., strain DS 1800, deposited on Oct. 1, 1981 at the Deutsche Sammlung von Mikroorganismen, Mascheroder Weg 1B, D-3300 Braunschweig FRG, in accordance with the provisions of the Budapest Treaty on the International Recognition of the Deposit of Microorganisms for the Purposes of Patent Procedure (the Budapest Treaty).

In still a further aspect, the cellulase enzymes useful herein can be defined, in addition to the screening test, as endoglucanase enzymes which have the amino acid sequence shown in the appended Sequence Listing SEQ ID NO: 4, or a homologue thereof (as defined above) exhibiting endoglucanase activity. Said endoglucanase enzyme may be one produced by a species of Fusarium, such as *Fusarium oxysporum*, e.g. strain DSM 2672, deposited on Jun. 6, 1983 at the Deutsche Sammlung yon Mikroorganismen, Mascheroder Weg 1B, D-3300 Braunschweig, FRG, in accordance with the provisions of the Budapest Treaty.

Furthermore, it is contemplated that homologous endoglucanases may be derived from other microorganisms producing cellulolytic enzymes, e.g. species of Tricboderma, Myceliophthora, Phanerochaete, Schizophylum, Penicillium, Aspergillus, and Geotricum.

For industrial production of the cellulase preparation herein, however, it is preferred to employ recombinant DNA techniques or other techniques involving adjustements of fermentations or mutation of the microorganisms involved to ensure overproduction of the desired enzymatic activities. Such methods and techniques are known in the art and may readily be carried out by persons skilled in the art.

The endoglucanase component may thus be one which is produced by a method comprising cultivating a host cell transformed with a recombinant DNA vector which carries a DNA sequence encoding said endoglucanase component or a precursor of said endoglucanase component as well as DNA sequences encoding functions permitting the expression of the DNA sequence encoding the endoglucanase component or precursor thereof, in a culture medium under conditions permitting the expression of the endoglucanase component or precursor thereof and recovering the endoglucanase component from the culture.

DNA constructs comprising a DNA sequence encoding an endoglucanase enzyme as described above, or a precursor form of the enzyme, include the DNA constructs having a DNA sequence as shown in the appended Sequence Listings SEQ ID NO: 1 or SEQ ID NO: 3, or a modification thereof. Examples of suitable modifications of the DNA sequence are nucleotide substitutions which do not give rise to another amino acid sequence of the endoglucanase, but which correspond to the codon usage of the host organism into which the DNA construct is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides at either end of the sequence, or deletion of one or more nucleotides at either end or within the sequence.

DNA constructs encoding endoglucanase enzymes useful herein may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

A DNA construct encoding the endoglucanase enzyme or a precursor thereof may, for instance, be isolated by establishing a cDNA or genomic library of a cellulase-producing microorganism, such as *Humicola insolens*, DSM 1800, and screening for positive clones by conventional procedures such as by hybridization using oligonucleotide probes sythesized on the basis of the full or partial amino acid sequence of the endoglucanase in accordance with standard techniques (cf. Sambrook et al, *Molecular Cloning: A Laboratory Manual*, 2nd Ed. Cold Spring Harbor, 1989), or by selecting for clones expressing the appropriate enzyme activity (i.e. CMC-endoase activity as defined above), or by selecting for clones producing a protein which is reactive with an anti-body against a native cellulase (endoglucanase)

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or R. K. Saiki et al, *Science* 239, 1988, pp. 487–491.

Recombinant expression vectors into which the above DNA constructs are inserted include any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into wich it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., op.cit.).

Host cells which are transformed with the above DNA constructs or the above expression vectors may be for instance belong to a species of Aspergillus, most preferably *Aspergillys oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Industri A/S), the contents of which are hereby incorporated by reference. The host cell may also be a yeast cell, e.g. a strain of *Saccharomyces cerevisiae*.

Alternatively, the host organism may be a bacterium, in particular strains of Streptomyces and Bacillus, and *E. coli*. The transformation of bacterial cells may be performed according to conventional methods, e.g. as described in Sambrook et al., *Molecular Cloning: A Laboratory Manual*, Cold Spring Harbor, 1989.

The screening of appropriate DNA sequences and construction of vectors may also be carried out by standard procedures, cf. Sambrook et al., op.cit.

The medium used to cultivate the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide endoglucanases of a high purity.

The level in the present composition of cellulase described above should be such that the amount of enzyme protein to be delivered in the wash solution is from 0.005 to 40 mg/liter of wash solution, preferably 0.01 to 10 mg/liter of wash solution.

The Softening Clay

One essential component of the present detergent compositions is a softening clay.

Any clay used in the art or mixtures thereof can be used in the present invention. Preferred examples have been disclosed in GB 1.400.898 or U.S. Pat. No. 5,019,292.

Included among such clays are various heat-treated kaolins and various multi-layer smectites. As known from the art, preferred smectite clays exhibit a cation-exchange capacity of at least 50 meq per 100 grams of clay, which corresponds to a layer charge of 0.2 to 0.6.

Further preferred are clays which have a particle size in the 5–50 micrometer range.

Additionally preferred smectite clays are hectorite clays of the general formula

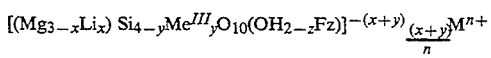

wherein y=0; or, if y≠0, $Me^{III}$ is Al, Fe, or B; $M^{n+}$ is a monovalent (n=1) or divalent (n=2) metal ion, for example selected from Na, K, Mg, Ca, Sr. The value of (x+y) is the layer charge of the hectorite clay. The hectorite clays suitable for the detergent compositions of the present invention have a layer charge distribution such that at least 50% is in the range of from 0.23 to 0.31.

Preferred are hectorite clays of natural origin having a layer charge distribution such that at least 65% is in the range of from 0.23 to 0.31.

Specific non-limiting examples of fabric softening smectite clay minerals are:
Sodium Montmorillonite
  Borck$^{(R)}$
  Volclay BC$^{(R)}$
  Gelwhite GP$^{(R)}$
  Thixo-Jel$^{(R)}$
  Ben-A-Gel$^{(R)}$
Sodium Hectorite
  Veegum F$^{(R)}$
  Laponite SP$^{(R)}$
Sodium Saponite
  Barasym NAS 100$^{(R)}$
Calcium Montmorillonite
  Soft Clark$^{(R)}$
  Gelwhite L$^{(R)}$
  Imvite K$^{(R)}$
  CSM-Clay $^{(R)}$ from Kimoulos
Lithium Hectorite
  Barasym LIH 200$^R$ The amount of softening clay useful in the present invention depends upon the form of the detergent composition. In general, it can range from lower limits of 0.5%, 1% or 8% to upper limits of 50%, 20% or 15%.

PREFERRED OPTIONAL INGREDIENTS

Clay flocculating agents are not commonly used in fabric treatment compositions. On the contrary, one is inclined to use clay dispersants, which aid in removing clay stains from fabrics. Clay flocculating agents are, however, very well known in other industries like oil well drilling, and for ore flotation in metallurgy. Most of these materials are fairly long chain polymers and copolymers derived from such monomers as ethylene oxide, acrylamide, acrylic acid, dimethylamino ethyl methacrylate, vinyl alcohol, vinyl pyrrolidone, ethylene imine. Gums, like guar gum, are suitable as well.

Preferred are polymers of ethylene oxide, acryl amide, or acrylic acid. It has been found that these polymers dramatically enhance the deposition of a clay if their molecular weights (weight average) are in the range of from 100,000 to 10 million. Preferred are such polymers having a (weight average) molecular weight of from 150.000 to 5 million, more preferably from 150,000 to 800,000.

The most preferred polymer is poly-(ethylene-oxide). Molecular weight distributions can be readily determined using gel permeation chromatography, against standards of poly-(ethylene-oxide) of narrow molecular weight distributions.

The amount of clay flocculating agent, expressed as percent of the clay, ranges from 0% to 20%. For clay flocculating agents having a (weight average) molecular weight of less than 800,000, the preferred amount is from 2% to 20% of the clay. For (weight average) molecular weight above 800,000 the preferred amount is from 0.005% to 2% of the clay.

Another preferred optional ingredient is substituted polysiloxane the amount of siloxane ranges from 0% to 50% by weight of the clay, preferably from 0.1% to 20%, most preferably from 1.0% to 10%.

The siloxanes useful in the present invention can be described as softening, straight or branched, organofunctional polydi-$C_{1-4}$-alkyl siloxane having the general formula:

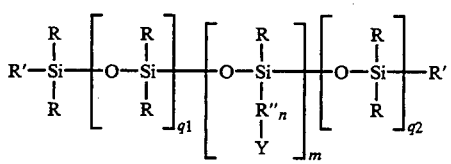

wherein

R is $C_{1-4}$-alkyl;

R' is R or a polyether of $(C_{2-3}\text{-oxides})_{1-50}$, with a capping group of H or R;

R" is branched or straight $C_{1-4}$-alkyl;

$q_1$ and $q_2$ are integers;

m and $(q_1+q_2)$ are integers from 4 to 1700;

n is an integer from 0 to 6;

Y is a polyether of $(C_{2-3}\text{-oxides})_k$, where k has an average value from 7 to 100, with a capping group of H or $C_{1-4}$-alkyl;

or Y is:

whereby

X and V are selected from —H;
—$C_{1-30}$-alkyl, —C-aryl;
—$C_{5-6}$-cycloalkyl; —$C_{1-6}$—$NH_2$;
—COR; with the proviso that the nitrogen can be quaternized such as to represent:

whereby

W can be selected from X and V.

or Y is

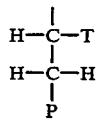

whereby

T and P are selected from —H, —COOH, —CO—O—$C_{1-2}$-alkyl, or epoxy-$C_{5-6}$-cycloalkyl Preferred siloxanes of said general formula are characterized by $(q_1+q_2)$ being an integer from 50 to 1500 and m being an integer from 4 to 100.

The most preferred siloxanes of said general formula are characterized by either of the following R, R' is methyl and R" is propyl and $(q_1+q_2)$ is 329 and m is 21 and n is 1 and y is a polyether consisting of 12 ethyl oxides and an acetic acid capping group or R, R' is methyl and R" is propyl and $(q_1+q_2)$ is 485 and m is 15 and n is 1 and y is a polyether consisting of 12 ethyl oxides and acetic acid capping group or R, R' is methyl and R" is methyl-2-propyl $(q_1+q_2)$ is 1470 and m is 30 and n is 1 and y is an -(amino ethyl)amine.

The detergent compositions of the present invention can be provided in liquid form as an aqueous dispersion. If in liquid form the detergent composition preferably further comprises an antisettling agent together with a softening clay, siloxane and clay flocculating agent.

A suitable antisettling agent must provide a fully activated support matrix to suspend particles within the liquid detergent composition.

Particles in this sense are granules or droplets of suspendable size for the desired properties of the liquid detergent composition. Usually the particle size will be less than 200 micrometers. The individual particles can comprise one or more of the essential or optional compounds of the detergent composition.

Finally, an acceptable antisettling agent must not adversely effect the viscosity, elasticity or aesthetics of the product.

These antisettling agents, or mixtures thereof, are used in the compositions of the present invention at levels of from 0.25% to 5%.

Organophillic quaternized ammonium-clay compounds for example of the Bentone$^R$ family of clays and also fumed silicas are examples of antisettling agents suitable for use in the present invention. Bentone$^R$ rheological additives are described as the products of a clay which contains a negative layer-lattice and an organic compound which contains a cation and at least one alkyl group containing at least 10 carbon atoms. Bentones$^R$ have the property of swelling in certain organic liquids. Organophillic quaternized ammonium-clay compounds are preferred antisettling agents as described in U.S. Pat. No. 4,287,086.

Fumed silicas also provide excellent antisettling characteristics to the compositions of the present invention. Fumed silicas are generally defined as a colloidal form of silica made by combustion of silicon tetrachloride in a hydrogen-oxygen furnace. Fumed silicas are normally used as thickener, thixotropic and reinforcing agents in inks, resins, rubber, paints and cosmetics. CAB-O-SIL$^{(R)}$ fumed silicas are suitable antisettling agents for use in this invention. Mixtures of Bentone$^{(R)}$ clays, fumed silicas or cellulosic suspending agents are also suitable antisettling agents.

The rheological characteristics of the resulting liquid compositions are very important to a commercially acceptable product. A liquid which can be described as stringy (i.e., elastic), thick or lumpy is undesirable. The antisettling agents described above avoid these undesirable rheological properties while maintaining a pourable, homogeneous product with good consumer appeal. A viscosity in the range of from about 100 to about 1000 kg/(ms) is desirable.

It is also desirable for the liquid composition to exhibit plastic rheology. Materials that exhibit plastic flow characteristics will flow only after an applied shearing stress exceeds a critical minimum value.

OPTIONAL INGREDIENTS

The present compositions will typically include optional ingredients that normally form part of detergent compositions. Antiredeposition and soil suspension agents, optical brighteners, bleaches, bleach activators, suds suppressors, anticacking agents, dyes and pigments are examples of such optional ingredients and can be added in varying amounts as desired.

Antiredeposition and soil suspension agents suitable herein include cellulose derivatives such as methylcellulose, carboxymethylcellulose and hydroxyethylcellulose. These materials are normally used at levels of from 0.5% to 10% by weight, more preferably from 0.75% to 8%, most preferably from 1% to 6% by weight of the composition. They can be used in granular detergent compositions but also to supplement the above-mentioned suspending agents for liquid detergent compositions.

Preferred optical brighteners are anionic in character, examples of which are disodium 4,4$^1$-bis-(2-diethanolamino-4-anilino-s-triazin-6-ylamino)stilbene-2:2$^1$disulphonate, disodium 4, -4$^1$-bis-(2-morpholino-4-anilino-s-triazin-6-ylaminostilbene-2:2$^1$-disulphonate, disodium 4,4$^1$-bis-(2,4-dianilino-s-triazin-6-ylamino)stilbene-2:2$^1$-disulphonate, monosodium 4$^1$,4$^{11}$-bis-(2,4-dianilino-s-triazin-6ylamino)stilbene-2-sulphonate, disodium 4,4$^1$-bis-(2-anilino-4-(N-methyl-N-2-hydroxyethylamino)-s-triazin-6-ylamino)stilbene-2,2$^1$-disulphonate, disodium 4,4$^1$-bis-(4-phenyl-2,1,3-triazol-2-yl)-stilbene-2,2$^1$disulphonate, disodium 4,4$^1$bis(2-anilino-4-(1-methyl-2-hydroxyethylamino)-s-triazin-6-ylamino)stilbene-2,2$^1$disulphonate and sodium 2(stilbyl-4$^{11}$-(naphtho-1$^1$,2$^1$:4,5)-1,2,3-triazole-2$^{11}$-sulphonate.

Any particulate inorganic perhydrate bleach can be used, in an amount of from 3% to 40% by weight, more preferably from 8% to 25% by weight and most preferably from 12% to 20% by weight of the compositions. Preferred examples of such bleaches are sodium perborate monohydrate and tetrahydrate, percarbonate, and mixtures thereof.

Another preferred separately mixed ingredient is a peroxy carboxylic acid bleach percursor, commonly referred to as a bleach activator, which is preferably added in a prilled or agglomerated form in granular detergents. Examples of suitable compounds of this type are disclosed in British Patent Nos. 1586769 and 2143231 and a method for their formation into a prilled form is described in European Published Patent Application No. 0 062 523. Preferred examples of such compounds are tetracetyl ethylene diamine and sodium 3,5,5trimethyl hexanoyloxybenzene sulphonate.

Bleach activators are normally employed at levels of from 0.5% to 10% by weight, more frequently from 1% to 8% and preferably from 2% to 6% by weight of the composition.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

As mentioned above, useful silicone suds controlling agents can comprise a mixture of an alkylated siloxane, of the type referred to hereinbefore, and solid silica. Such mixtures are prepared by affixing the silicone to the surface of the solid silica. A preferred silicone suds controlling agent is represented by a hydrophobic silanated (most preferably trimethyl-silanated) silica having a particle size in the range from 10 millimicrons to 20 millimicrons and a specific surface area above 50 m$^2$/g intimately admixed with dimethyl silicone fluid having a molecular weight in the range from about 500 to about 200,000 at a weight ratio of silicone to silanated silica of from about 1:1 to about 1:2.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2,646,126 published Apr. 28, 1977. An example of such a compound is DC-544, commercially availably from Dow Corning, which is a siloxane/glycol copolymer.

The suds suppressors described above are normally employed at levels of from 0.001% to 2% by weight of the composition, preferably from 0.01% to 1% by weight. The incorporation of the suds modifiers is preferably made as separate particulates, and this permits the inclusion therein of other suds controlling materials such as C20-C24 fatty acids, microcrystalline waxes and high MW copolymers of ethylene oxide and propylene oxide which would otherwise adversely affect the dispersibility of the matrix. Techniques for forming such suds modifying particulates are disclosed in the previously mentioned Bartolotta et al U.S. Pat. No. 3,933,672.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers as well as the previously mentioned homo- or co-polymeric polycarboxylate polymers are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4,116,885 and 4,711,730 and European Published Patent Application No. 0 272 033. A particular preferred polymer in accordance with EP-A-0 272 033 has the formula

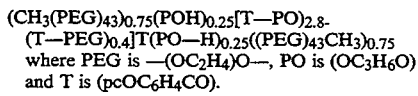
where PEG is —($OC_2H_4$)O—, PO is ($OC_3H_6O$) and T is (pc$OC_6H_4$CO).

Certain polymeric materials such as polyvinyl pyrrolidones typically of MW 5000–20000, preferably 10000–15000, also form useful agents in preventing the transfer of labile dyestuffs between fabrics during the washing process.

Other fabric softening agents can also be incorporated into detergent compositions in accordance with the present invention. These agents may be inorganic or organic in type. Organic fabric softening agents include the water-insoluble tertiary amines as disclosed in GB-A-1514276 and EP-B-0 011 340 and their combination with mono C12–C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Organic fabric softening agents such as the water-insoluble tertiary amines or di-long-chain amide materials are incorporated at levels of from 0.5% to 5% by weight, normally from 1% to 3% by weight whilst the high molecular weight polyethylene oxide materials and the water-soluble cationic materials are added at levels of from 0.1% to 2%, normally from 0.15% to 1.5% by weight. For granular detergents these materials are normally added to the spray dried portion of the composition, although in some instances it may be more convenient to add them as a dry mixed particulate, or spray them as a molten liquid on to other solid components of the composition.

Enzymes other than the specific cellulase preparation herein can be present in the composition herein, such as proteases, lipuses and amylases.

MAKING PROCESS

Compositions according to the present invention, depending on whether they are liquid or granular, can be made via a variety of methods including liquid mixing according to a temperature and pH time profile, melting, dissolving, dry mixing, spray drying, agglomeration and granulation and combinations of any of these techniques.

A preferred method of making granular detergent compositions, particularly those having a high density (compact) herein involves a combination of spray drying, agglomeration in a high speed mixer and dry mixing.

A first granular component containing a relatively insoluble anionic surfactant is spray dried and part of the spray dried product is diverted and subjected to a low level of nonionic surfactant spray-on before being reblended with the remainder. A second granular component is made by dry neutralisation of an anionic surfactant acid using sodium carbonate as the neutralising agent in a continuous high speed blender such as a Lodige KM mixer. The first and second components together with other dry mix ingredients such as the carboxylate chelating agent, inorganic peroxygen bleach, bleach activator, soil suspension agent, silicate and the polycarboxylate polymer and enzyme are then fed to a conveyor belt from which they are transferred to a horizontally rotating drum in which perfume and silicone suds suppressor are sprayed-on to the product. In highly preferred compositions, a further drum mixing step is employed in which a low (approx. 2%) level of finely divided crystalline aluminosilicate is introduced to increase density and improve granular flow characteristics.

For a preferred method of making the liquid detergent compositions according to the present invention, it has been found that liquid detergent compositions are advantageously prepared when pH and temperature are always kept constant or are reduced during production of the liquid detergent.

EXAMPLES

The following examples illustrate the invention and facilitate its understanding.

The abbreviations for the individual ingredients have the following meaning:

LAS: sodium salt of linear dodecyl benzene sulfonate
TAS: sodium salt of tallow alcohol sulfate
AS: sodium salt of alkyl ($C_{14}$–$C_{15}$) sulfate
AO: $C_{12}$–$C_{14}$ alkyl dimethylamine oxide
FA25E7: fatty alcohol ($C_{12}$–$C_{15}$) ethoxylated with about 7 moles of ethylene oxide
CAT: $C_{12}$–$C_{14}$ trimethyl(or dimethyl (hydroxyethyl)) ammonium chloride
Clay: montmorillonite clay
Zeolite 4A: sodium salt of zeolite 4A with average particle size between 1–10 micrometer
SKS-6: crystalline layered silicate (Hoechst)
AA/MA: copolymeric polycarboxylate polymer of acrylic acid and maleic acid
PAP: polyacrylic polymer, MW 1000→10000
CMC: carboxymethylcellulose
Phosphonate: sodium salt of ethylenediamine tetramethylene phosphonic acid
AOS: A-Olefin ($C_{12}$–$C_{18}$) sulfonate, sodium salt
NMN: N-methyl N-1-deoxyglycithyl ($C_{12}$–$C_{18}$) alkyl amide
EDTA: sodium salt of ethylenediamine tetra acetate
PB1: NaBO2.H2O2
PB4: NaBO2.H2O2.3H2O
TAED: tetra acetyl ethylene diamine
NOBS: -nonanoyl oxybenzene sodium sulfonate
P.A.: sulphonated zinc phthalocyanine Silicate (R=n): $SiO_2/Na_2O$=n
Amylase: Termamyl 60T (Novo-Nordisk)
Lipase: Lipolase 100T (Novo-Nordisk)
Protease: Savinase 4T (Novo-Nordisk)
SP300: Celluzyme SP300—(prior art cellulase by Novo Nordisk)
43 kD: about 43 kD cellulase according to the cellulase defined in the present invention
SSS: Suds Suppressing System (silica/silicone mixture)
NTA: Sodium salt of nitrilotriacetate
TAE-11: Tallow alcohol ethoxylated with about 11 moles of ethylene oxide
DTMA: Ditallow methyl amine
CFA: Coconut fatty acid
HFA: Hydrogenated C16–22 fatty acid To facilitate a softness comparison, the following test procedure was used:

3.5 kg of clean fabric laundry loads are washed in an automatic drum washing machine Miele$^R$ 423 at 60° C.

for 1.5 hours. The hardness of the water was 2.5 mmol of $Ca^{2+}/Mg^{2+}$ per liter and the composition concentration was 0.7% in the wash liquid. For softness evaluation swatches of terry towel softness tracers were added. The softness tracers were line dried prior to assessment of softness.

Evaluation of test results was done with two methods:

Comparative softness assessment was done by expert judges using a scale of 0 to 4 panel-score-units (PSU). In this scale 0 is given for no difference and 4 is given for maximum difference. In this scale 0 is given for no difference and 4 is given for maximum difference. Softness was assessed after eight wash cycles on aged terry swatches, as defined below.

Another softness assessment is done by using a laboratory softness measurement device, the Kawabata KES-FB1 machine, Kato Tech Corporation Ltd. Japan.

In this machine the softness tracers are placed between two clamps which are movable relative to each other. Comparative softness was measured after eight wash cycles by shear hysteresis at 5 degree angle (2 HG 5). A decrease in shear hysteresis reflects increased softness performance. Measurements are means of 3 user aged terry swatches. User aged is defined by a minimum of 10 normal washes.

EXAMPLES I TO IV:

A basic detergent composition is evaluated to indicate the unexpected effect of higher-than-additive softening performance of the selected compositions vs. closest prior art which is considered to be EP-A-177 165.

Full test results of Examples I to IV can be found in Table III. The detergent composition used is based on composition I of Table V. In the last two columns of Table III the dependence of the overall superiority of the present invention on the selected cellulase in combination with softening clay can be seen. However, this is even clearer exemplified in the following examples.

Examples V to VIII

A basic detergent composition, composition II of Table V, is evaluated in above described test procedure and measured with the Kawabata machine.

The reduction, expressing the softening, of the measurement for clay alone is 5%, for high activity cellulase alone is 15%. The expected value for the combination should therefore be about 20% which surprisingly is surpassed by this combination and reaches 39%, i.e. about twice the expected value.

Compositions III through XII of Table V provide examples which include softening clay as well as high activity cellulase and have been found to perform in accordance with the objectives of the present invention, providing especially good fabric treatment performance.

Clay in these compositions was montmorillonite or hectorite clay at levels of 10% for compositions III to VI and IX, 12% for compositions VII, VIII and X and 8.6% for compositions XI and XII. Composition IX also contained an anti-settling agent of the Bentone$^{(R)}$ family such that settling of the clay is prevented. The cellulase is generally added from 0.01 to 10.0, preferably 0.1 to 0.5, mg/liter of wash solution.

TABLE III

Compositions and Results of Example I to IV
The test wash solution contained
0.7% by weight detergent I (DI) of Table V. If present clay was added at 0.0875% by weight of the wash solution and cellulase was added to provide $2200 \times 10^{-6}\%$ by weight of the wash solution of cellulase protein for SP300 and $24 \times 10^{-6}\%$ by weight of the wash solution of cellulase for 43kD. These levels were selected to have an equal CMC-endoase activity of 105 CEVU per liter wash solution.

| Example | Test Pairing | PSU | ΔPSU In a clay context | ΔPSU in a cellulase context |
|---|---|---|---|---|
| I | DI + SP300 vs DI | 0.5 | Example II − Example I = −0.2 | Example III − Example I = +0.7 |
| II | DI + SP300 + clay vs DI + clay | 0.3 | | |
| III | DI + 43kD vs. DI | 1.2 | Example IV − Example III = +0.8 | Example IV − Example II = +1.7 |
| IV | DI + 43kD + clay vs DI + clay | 2.0 | | |

Examples I and II supports the prior art theory of not creating an adverse effect by combining softening clay with cellulase. However, the result also indicates that this does not provide any benefit. In fact, since the combination of clay and cellulase of this prior art disclosure provides no benefit it may be speculated that the ecological and economical burden it creates, is the reason for its lack of commercial success.

Examples III and IV, IV being according to the invention, clearly indicate that the performance of softening clay and cellulase provides more-than-additive benefits.

From Example II the benefit of clay, in a prior art cellulase environment can be found to be 0.3 PSU. Turning to Example IV, which is tested in a 43 kD cellulase environment, the result jumps to more than 6 times that number, reaching 2 PSU.

TABLE IV

| | Synergetic effect of clay and cellulase | | | |
|---|---|---|---|---|
| Example | V | VI | VII | VIII |
| Wash solution contained (except water) | | | | |
| Detergent*, composition II of Table V | 0.7% | 0.7% | 0.7% | 0.7% |
| 43kD** | | | 40 | 40 |
| clay* | | 0.035% | | 0.035% |
| Test results: | | | | |
| Kawabata Softness in [gf/cm] | 7.19 | 6.8 | 6.11 | 4.39 |
| Index of reduction | reference | 5% | 15% | 39% |

*by weight of wash solution
**protein in $10^{-6}\%$ by weight of wash solution

TABLE V

Detergent Compositions
(all percentages in weight of total composition)

| Composition | I | II | III | IV | V | VI |
|---|---|---|---|---|---|---|
| Form, density (liquid = l, granular = g, compacted = c) | g | g | g | g | g | g |
| LAS | 7.6 | 7.6 | 7 | 5 | 4 | — |
| TAS | 1.86 | 1.86 | — | 2 | — | — |
| AS | — | — | — | — | 3 | 4 |
| TAE-11 | 0.98 | 0.98 | 0.5 | — | — | — |
| CAT | 1.46 | 1.46 | — | — | 1.5 | 1.5 |
| FA25E7 | 1.37 | 1.37 | — | — | — | 0.5 |
| AOS | — | — | — | — | — | 0.5 |
| NMN | — | — | 5 | 5 | 6 | 5 |
| HFA | — | — | 0.5 | — | — | — |
| Na-tripolyphosphate | — | — | 24 | — | — | 25 |
| Na citrate/citric acid | 5.3 | 5.3 | — | 5 | 5 | — |
| Zeolite 4A | 18.5 | 18.5 | — | 20 | 20 | — |
| AA/MA | 3.4 | 3.4 | 2 | — | — | 3 |
| Phosphonate | 0.38 | 0.38 | — | — | — | — |
| Mg SO4 | 0.4 | 0.4 | — | — | — | — |
| Oleic fatty acid | — | — | — | — | — | — |
| C14–16 alkyl succinate | — | — | — | — | — | — |
| 1,2 propandiol | — | — | — | — | — | — |
| Ethanol | — | — | — | — | — | — |
| PB1 | 11.4a | 11.4 | 15 | 15 | 18 | 15 |
| TAED | 3.4 | 3.4 | 3 | 3 | — | 3 |
| P.A. | $2 \times 10^{-3}$ | $2 \times 10^{-3}$ | — | — | — | — |
| Protease | 1.4 | 1.4 | 1.0 | — | 1.0 | — |
| Lipase | — | — | — | 0.2 | 0.2 | — |
| Amylase | — | — | — | 0.5 | 0.5 | — |
| Na-sulfate | — | — | 12. | 10 | 15 | 5 |
| Na-carbonate | 10.6 | 10.6 | 5 | 7 | — | 15 |
| Na-silicate | 3.9 | 3.9 | 4 | 4 | 4 | 4 |
| SSS | 1.88 | 1.88 | — | — | — | — |
| PAP | — | — | 1.5 | 0.3 | — | — |
| CMC | 0.34 | 0.34 | 0.3 | 0.3 | 0.3 | 0.3 |
| PE-oxide | — | — | 0.05 | 0.3 | — | 0.05 |
| Glycerol | 0.62 | — | — | — | — | — |
| Miscellaneous (Perfume, buffer, moisture) and/or water | Bal. to 100 | Bal. to 100 | Bal. to 100 | Bal. to 100 | Bal. to 100 | Bal. to 100 |

| Composition | VII | VIII | IX | X | XI | XII |
|---|---|---|---|---|---|---|
| Form, density (liquid = l, granular = g, compacted = c) | c | c | l | c | c | c |
| LAS | 8 | — | 10 | 8.20 | 6.50 | — |
| TAS | 2 | 2 | — | 2.65 | 3.25 | 3.9 |
| AS | — | 6 | 1 | — | — | — |
| TAE-11 | — | — | — | — | — | — |
| CAT | 1.5 | 1.5 | — | — | — | 2.45 |
| FA25E7 | — | — | — | — | 2.20 | 6.00 |
| Percarbonate | — | — | — | — | — | 12.00 |
| NMN | 5 | 5 | 7 | 3.00 | — | — |
| PB-4 | — | — | — | 3.55 | — | — |
| SKS-6 | — | — | — | — | — | 12.90 |
| Na citrate/citric acid | — | 6 | 2 | 23.50 | 12.00 | 15.00 |
| Zeolite 4A | 23 | 19 | — | — | 16.00 | 15.65 |
| AA/MA | 5 | 4 | — | 3.50 | 3.45 | 3.45 |
| Phosphonate | — | — | — | 0.3 | — | — |
| EDTA | — | — | — | — | 0.32 | 0.32 |
| Oleic fatty acid | — | — | 1 | — | — | — |
| C14–16 alkyl succinate | — | — | 10 | — | — | — |
| 1,2 propandiol | — | — | 3 | — | — | — |
| Ethanol | — | — | 7 | — | — | — |
| PB1 | 11 | 12 | — | 11.47 | 11.50 | — |
| TAED | 4 | 3 | — | 2.47 | 3.20 | — |
| P.A. | — | — | — | — | 0.003 | 0.003 |
| Protease | 1.0 | — | 1.0 | 1.05 | 1.40 | 1.40 |
| Lipase | 0.2 | 0.2 | 0.3 | — | 0.30 | 0.30 |
| Amylase | 0.3 | — | 0.3 | — | — | — |
| Na-sulfate | — | — | — | 2.23 | 3.45 | 3.45 |

TABLE V-continued

Detergent Compositions
(all percentages in weight of total composition)

| | | | | | | |
|---|---|---|---|---|---|---|
| Na-carbonate | 11 | 11 | — | 2.50 | 9.90 | 9.90 |
| Na-silicate | 4 | 3 | — | 2.30 | 2.50 | 2.50 |
| SSS | — | — | — | 0.50 | 0.50 | 0.50 |
| PAP | — | — | — | 1.50 | — | — |
| CMC | 0.3 | 0.3 | — | 0.25 | — | — |
| PE-oxide | 0.3 | 0.3 | — | — | — | — |
| NOBS | — | — | — | 2.00 | — | — |
| Miscellaneous (Perfume, buffer, moisture, and/or water) | Bal. to 100 | Bal. to 100 | Bal. to 100 | Bal. to 100 | Bal. to 100 | Bal. to 100 |

We claim:

1. A detergent composition comprising a surface active agent, a builder system, a softening clay, a clay flocculating agent in an amount from about 0.005% to 20% by weight of said clay, and a cellulase characterized in that said cellulase provides at least 10% removal of immobilized, radio-active labelled carboxylmethylcellulose according to the C14CMC-method at $25 \times 10^{-6}\%$ by weight of cellulase protein in the laundry test solution.

2. A detergent composition according to claim 1 characterized in that the cellulase compound consists essentially of a homogenous endoglucanase component which is immunoreactive with an antibody raised against a highly purified, about 43 kD cellulase derived from *Humicola insolens*, DSM 1800.

3. A detergent composition according to claim 2 wherein the endoglucanase component of said cellulase has an isoelectric point of about 5.1.

4. A detergent composition according to claim 2 wherein said endoglucanase component is produced by a method comprising cultivating a host cell transformed with a recombinant DNA vector carrying a DNA sequence encoding said endoglucanase component or a precursor of said endoglucanase component, as well as DNA sequences encoding functions permitting the expression of the DNA sequence encoding the endoglucanase component, or a precursor thereof, in a culture medium under conditions permitting the expression of the endoglucanase component or precursor thereof and recovering the endoglucanase component from the culture.

5. A detergent composition according to claim 1 characterized in that the cellulase compound is an endoglucanase enzyme having the amino acid sequence shown in the appended listing SEQ ID NO: 2.

6. A detergent composition according to claim 1 wherein said endoglucanase enzyme is produced by *Fusarium oxysporum*.

7. A detergent composition according to claim 6 characterized in that the cellulase compound is an endoglucanase enzyme having an amino acid sequence shown in the appended sequence listing SEQ ID NO: 4.

8. A detergent composition according to claim 5, 7 or 6 wherein said enzyme is produced by a DNA construct comprising a DNA sequence encoding the enzyme.

9. A detergent composition according to claim 8 wherein the DNA sequence is shown as appended sequence listing SEQ ID NO: 1 or SEQ ID NO: 3.

10. A detergent composition according to claims 1, 2, 3, 4, or 5 wherein said host cell is a strain of a fungus such as Tricloderuca or Aspergillus, preferably *Aspergillus oryzae* or *Asperugillus niger*, or a yeast cell belonging to a strain of Hansenula or Saccharomyces, e.g. a strain of *Saccachomyces cerevisae*.

11. A detergent composition according to claims 1, 2, 3, 4, or 5 wherein said host cell is a strain of a bacterium, e.g. Bacillus, Streptomyces or *E. coli*.

12. A detergent composition according to claim 1 characterized in that said cellulase is present in an amount such that the amount of enzyme protein delivered to the wash solution is 0.005 to 40 mg/liter of wash solution, preferably 0.01 to 10 mg/liter of wash solution.

13. A detergent composition according to claim 1 characterized in that the amount of softening clay is from 0.5% to 50%, by weight of the detergent composition.

14. A detergent composition according to claim 1 or 13 characterized in that said softening clay is a smectite, clay with a cation exchange capacity of at least 50 meq/100 g.

15. A detergent composition according to claim 1 or 13 characterized in that it further comprises up to 50% of said clay of said detergent composition of a substituted polysiloxane.

16. A detergent composition according to claim 1 which is a granular detergent.

17. A detergent composition according to claim 16 wherein said composition contains no more than 15% by weight of inorganic filler salt and having a density of 550 to 950 g/liter of composition.

18. A detergent composition according to claim 17 wherein said inorganic filler salt is selected from alkali and alkaline-earth metal salts of sulphate and chloride.

19. A detergent composition in accordance with claim 17 which does not contain more than 10% by weight of inorganic filler salt.

20. A detergent composition in accordance with claim 19 which does not contain more than 5% by weight of inorganic filler salt.

21. A detergent composition according to claim 17, 18, 19, or 20 which has a density of 650 to 850 g/liter.

22. A detergent composition according to claim 1 which is substantially free of phosphate compounds and wherein said builder comprises polycarboxylate polymers and further comprises compounds selected from aluminosilicate ion exchangers, citrates, carbonates and mixtures thereof.

23. A detergent composition according to claim 13 wherein the amount of softening clay is from 5% to 20% by weight.

24. A detergent composition according to claim 23 wherein in amount of softening clay is from 8% to 15% by weight.

25. A detergent composition according to claim 14 wherein the smectite clay is a montmorillonite or hectorite clay.

26. A detergent composition according to claim 15 wherein said substituted polysiloxane is present at a level of 0.1% to 20% by weight of said clay.

* * * * *

UNITED STATES PATENT AND TRADEMARK OFFICE
CERTIFICATE OF CORRECTION

PATENT NO. : 5,443,750
DATED : August 22, 1995
INVENTOR(S) : André Convents et al.

It is certified that error appears in the above-identified patent and that said Letters Patent is hereby corrected as shown below:

Title page:
Item: [75], change "all of Germany" to --all of Belgium--.

In Column 33, line 68, change "clay, and" to --clay and--.

In Column 35, line 41, change "listing" to --listings--.

Signed and Sealed this

Tenth Day of September, 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1060 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 10..924

( x i ) SEQUENCE DESCRIPTION: SEQ ID NO:1:

```
GGATCCAAG ATG CGT TCC TCC CCC CTC CTC CCG TCC GCC GTT GTG GCC            48
          Met Arg Ser Ser Pro Leu Leu Pro Ser Ala Val Val Ala
            1               5                  10

GCC CTG CCG GTG TTG GCC CTT GCC GCT GAT GGC AGG TCC ACC CGC TAC          96
Ala Leu Pro Val Leu Ala Leu Ala Ala Asp Gly Arg Ser Thr Arg Tyr
         15                  20                  25

TGG GAC TGC TGC AAG CCT TCG TGC GGC TGG GCC AAG AAG GCT CCC GTG         144
Trp Asp Cys Cys Lys Pro Ser Cys Gly Trp Ala Lys Lys Ala Pro Val
 30                  35                  40                  45

AAC CAG CCT GTC TTT TCC TGC AAC GCC AAC TTC CAG CGT ATC ACG GAC         192
Asn Gln Pro Val Phe Ser Cys Asn Ala Asn Phe Gln Arg Ile Thr Asp
                 50                  55                  60

TTC GAC GCC AAG TCC GGC TGC GAG CCG GGC GGT GTC GCC TAC TCG TGC         240
Phe Asp Ala Lys Ser Gly Cys Glu Pro Gly Gly Val Ala Tyr Ser Cys
                     65                  70                  75

GCC GAC CAG ACC CCA TGG GCT GTG AAC GAC GAC TTC GCG CTC GGT TTT         288
Ala Asp Gln Thr Pro Trp Ala Val Asn Asp Asp Phe Ala Leu Gly Phe
                         80                  85                  90

GCT GCC ACC TCT ATT GCC GGC AGC AAT GAG GCG GGC TGG TGC TGC GCC         336
Ala Ala Thr Ser Ile Ala Gly Ser Asn Glu Ala Gly Trp Cys Cys Ala
             95                 100                 105

TGC TAC GAG CTC ACC TTC ACA TCC GGT CCT GTT GCT GGC AAG AAG ATG         384
Cys Tyr Glu Leu Thr Phe Thr Ser Gly Pro Val Ala Gly Lys Lys Met
110                 115                 120                 125

GTC GTC CAG TCC ACC AGC ACT GGC GGT GAT CTT GGC AGC AAC CAC TTC         432
Val Val Gln Ser Thr Ser Thr Gly Gly Asp Leu Gly Ser Asn His Phe
                 130                 135                 140

GAT CTC AAC ATC CCC GGC GGC GGC GTC GGC ATC TTC GAC GGA TGC ACT         480
Asp Leu Asn Ile Pro Gly Gly Gly Val Gly Ile Phe Asp Gly Cys Thr
                     145                 150                 155

CCC CAG TTC GGC GGT CTG CCC GGC CAG CGC TAC GGC GGC ATC TCG TCC         528
Pro Gln Phe Gly Gly Leu Pro Gly Gln Arg Tyr Gly Gly Ile Ser Ser
             160                 165                 170
```

```
CGC AAC GAG TGC GAT CGG TTC CCC GAC GCC CTC AAG CCC GGC TGC TAC       576
Arg Asn Glu Cys Asp Arg Phe Pro Asp Ala Leu Lys Pro Gly Cys Tyr
    175             180                 185

TGG CGC TTC GAC TGG TTC AAG AAC GCC GAC AAT CCG AGC TTC AGC TTC       624
Trp Arg Phe Asp Trp Phe Lys Asn Ala Asp Asn Pro Ser Phe Ser Phe
190             195                 200                 205

CGT CAG GTC CAG TGC CCA GCC GAG CTC GTC GCT CGC ACC GGA TGC CGC       672
Arg Gln Val Gln Cys Pro Ala Glu Leu Val Ala Arg Thr Gly Cys Arg
                210                 215                 220

CGC AAC GAC GAC GGC AAC TTC CCT GCC GTC CAG ATC CCC TCC AGC AGC       720
Arg Asn Asp Asp Gly Asn Phe Pro Ala Val Gln Ile Pro Ser Ser Ser
                225                 230                 235

ACC AGC TCT CCG GTC AAC CAG CCT ACC AGC ACC AGC ACC ACG TCC ACC       768
Thr Ser Ser Pro Val Asn Gln Pro Thr Ser Thr Ser Thr Thr Ser Thr
            240                 245                 250

TCC ACC ACC TCG AGC CCG CCA GTC CAG CCT ACG ACT CCC AGC GGC TGC       816
Ser Thr Thr Ser Ser Pro Pro Val Gln Pro Thr Thr Pro Ser Gly Cys
    255                 260                 265

ACT GCT GAG AGG TGG GCT CAG TGC GGC GGC AAT GGC TGG AGC GGC TGC       864
Thr Ala Glu Arg Trp Ala Gln Cys Gly Gly Asn Gly Trp Ser Gly Cys
270             275                 280                 285

ACC ACC TGC GTC GCT GGC AGC ACT TGC ACG AAG ATT AAT GAC TGG TAC       912
Thr Thr Cys Val Ala Gly Ser Thr Cys Thr Lys Ile Asn Asp Trp Tyr
                290                 295                 300

CAT CAG TGC CTG TAGACGCAGG GCAGCTTGAG GGCCTTACTG GTGGCCGCAA           964
His Gln Cys Leu
            305

CGAAATGACA CTCCCAATCA CTGTATTAGT TCTTGTACAT AATTTCGTCA TCCCTCCAGG    1024

GATTGTCACA TAAATGCAAT GAGGAACAAT GAGTAC                              1060
```

( 2 ) INFORMATION FOR SEQ ID NO:2:

( i ) SEQUENCE CHARACTERISTICS:
        ( A ) LENGTH: 305 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ser Ser Pro Leu Leu Pro Ser Ala Val Ala Ala Leu Pro
 1               5                  10                  15

Val Leu Ala Leu Ala Ala Asp Gly Arg Ser Thr Arg Tyr Trp Asp Cys
                20                  25                  30

Cys Lys Pro Ser Cys Gly Trp Ala Lys Lys Ala Pro Val Asn Gln Pro
            35                  40                  45

Val Phe Ser Cys Asn Ala Asn Phe Gln Arg Ile Thr Asp Phe Asp Ala
        50                  55                  60

Lys Ser Gly Cys Glu Pro Gly Gly Val Ala Tyr Ser Cys Ala Asp Gln
 65                 70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160
```

```
Gly Gly Leu Pro Gly Gln Arg Tyr Gly Gly Ile Ser Ser Arg Asn Glu
            165                 170                 175
Cys Asp Arg Phe Pro Asp Ala Leu Lys Pro Gly Cys Tyr Trp Arg Phe
            180                 185                 190
Asp Trp Phe Lys Asn Ala Asp Asn Pro Ser Phe Ser Phe Arg Gln Val
            195                 200                 205
Gln Cys Pro Ala Glu Leu Val Ala Arg Thr Gly Cys Arg Arg Asn Asp
210                 215                 220
Asp Gly Asn Phe Pro Ala Val Gln Ile Pro Ser Ser Ser Thr Ser Ser
225                 230                 235                 240
Pro Val Asn Gln Pro Thr Ser Thr Ser Thr Ser Thr Ser Thr Thr
            245                 250                 255
Ser Ser Pro Pro Val Gln Pro Thr Thr Pro Ser Gly Cys Thr Ala Glu
            260                 265                 270
Arg Trp Ala Gln Cys Gly Gly Asn Gly Trp Ser Gly Cys Thr Thr Cys
            275                 280                 285
Val Ala Gly Ser Thr Cys Thr Lys Ile Asn Asp Trp Tyr His Gln Cys
            290                 295                 300
Leu
305
```

( 2 ) INFORMATION FOR SEQ ID NO:3:

( i ) SEQUENCE CHARACTERISTICS:
        ( A ) LENGTH: 1473 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 97..1224

( x i ) SEQUENCE DESCRIPTION: SEQ ID NO:3:

```
GAATTCGCGG CCGCTCATTC ACTTCATTCA TTCTTTAGAA TTACATACAC TCTCTTTCAA        60

AACAGTCACT CTTTAAACAA AACAACTTTT GCAACA ATG CGA TCT TAC ACT CTT        114
                                         Met Arg Ser Tyr Thr Leu
                                          1               5

CTC GCC CTG GCC GGC CCT CTC GCC GTG AGT GCT GCT TCT GGA AGC GGT        162
Leu Ala Leu Ala Gly Pro Leu Ala Val Ser Ala Ala Ser Gly Ser Gly
                10                  15                  20

CAC TCT ACT CGA TAC TGG GAT TGC TGC AAG CCT TCT TGC TCT TGG AGC        210
His Ser Thr Arg Tyr Trp Asp Cys Cys Lys Pro Ser Cys Ser Trp Ser
             25                  30                  35

GGA AAG GCT GCT GTC AAC GCC CCT GCT TTA ACT TGT GAT AAG AAC GAC        258
Gly Lys Ala Ala Val Asn Ala Pro Ala Leu Thr Cys Asp Lys Asn Asp
     40                  45                  50

AAC CCC ATT TCC AAC ACC AAT GCT GTC AAC GGT TGT GAG GGT GGT GGT        306
Asn Pro Ile Ser Asn Thr Asn Ala Val Asn Gly Cys Glu Gly Gly Gly
 55                  60                  65                  70

TCT GCT TAT GCT TGC ACC AAC TAC TCT CCC TGG GCT GTC AAC GAT GAG        354
Ser Ala Tyr Ala Cys Thr Asn Tyr Ser Pro Trp Ala Val Asn Asp Glu
                 75                  80                  85

CTT GCC TAC GGT TTC GCT GCT ACC AAG ATC TCC GGT GGC TCC GAG GCC        402
Leu Ala Tyr Gly Phe Ala Ala Thr Lys Ile Ser Gly Gly Ser Glu Ala
             90                  95                 100

AGC TGG TGC TGT GCT TGC TAT GCT TTG ACC TTC ACC ACT GGC CCC GTC        450
Ser Trp Cys Cys Ala Cys Tyr Ala Leu Thr Phe Thr Thr Gly Pro Val
        105                 110                 115

AAG GGC AAG AAG ATG ATC GTC CAG TCC ACC AAC ACT GGA GGT GAT CTC        498
Lys Gly Lys Lys Met Ile Val Gln Ser Thr Asn Thr Gly Gly Asp Leu
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | 120 |     |     |     |     | 125 |     |     |     |     | 130 |     |     |      |
| GGC | GAC | AAC | CAC | TTC | GAT | CTC | ATG | ATG | CCC | GGC | GGT | GGT | GTC | GGT | ATC  | 546 |
| Gly | Asp | Asn | His | Phe | Asp | Leu | Met | Met | Pro | Gly | Gly | Gly | Val | Gly | Ile  |
| 135 |     |     |     |     | 140 |     |     |     |     | 145 |     |     |     |     | 150  |
| TTC | GAC | GGC | TGC | ACC | TCT | GAG | TTC | GGC | AAG | GCT | CTC | GGC | GGT | GCC | CAG  | 594 |
| Phe | Asp | Gly | Cys | Thr | Ser | Glu | Phe | Gly | Lys | Ala | Leu | Gly | Gly | Ala | Gln  |
|     |     |     |     | 155 |     |     |     |     | 160 |     |     |     |     | 165 |      |
| TAC | GGC | GGT | ATC | TCC | TCC | CGA | AGC | GAA | TGT | GAT | AGC | TAC | CCC | GAG | CTT  | 642 |
| Tyr | Gly | Gly | Ile | Ser | Ser | Arg | Ser | Glu | Cys | Asp | Ser | Tyr | Pro | Glu | Leu  |
|     |     |     | 170 |     |     |     |     | 175 |     |     |     |     | 180 |     |      |
| CTC | AAG | GAC | GGT | TGC | CAC | TGG | CGA | TTC | GAC | TGG | TTC | GAG | AAC | GCC | GAC  | 690 |
| Leu | Lys | Asp | Gly | Cys | His | Trp | Arg | Phe | Asp | Trp | Phe | Glu | Asn | Ala | Asp  |
|     |     | 185 |     |     |     |     | 190 |     |     |     |     | 195 |     |     |      |
| AAC | CCT | GAC | TTC | ACC | TTT | GAG | CAG | GTT | CAG | TGC | CCC | AAG | GCT | CTC | CTC  | 738 |
| Asn | Pro | Asp | Phe | Thr | Phe | Glu | Gln | Val | Gln | Cys | Pro | Lys | Ala | Leu | Leu  |
|     | 200 |     |     |     |     | 205 |     |     |     |     | 210 |     |     |     |      |
| GAC | ATC | AGT | GGA | TGC | AAG | CGT | GAT | GAC | GAC | TCC | AGC | TTC | CCT | GCC | TTC  | 786 |
| Asp | Ile | Ser | Gly | Cys | Lys | Arg | Asp | Asp | Asp | Ser | Ser | Phe | Pro | Ala | Phe  |
| 215 |     |     |     | 220 |     |     |     |     | 225 |     |     |     |     | 230 |      |
| AAG | GTT | GAT | ACC | TCG | GCC | AGC | AAG | CCC | CAG | CCC | TCC | AGC | TCC | GCT | AAG  | 834 |
| Lys | Val | Asp | Thr | Ser | Ala | Ser | Lys | Pro | Gln | Pro | Ser | Ser | Ser | Ala | Lys  |
|     |     |     | 235 |     |     |     |     | 240 |     |     |     |     | 245 |     |      |
| AAG | ACC | ACC | TCC | GCT | GCT | GCT | GCC | GCT | CAG | CCC | CAG | AAG | ACC | AAG | GAT  | 882 |
| Lys | Thr | Thr | Ser | Ala | Ala | Ala | Ala | Ala | Gln | Pro | Gln | Lys | Thr | Lys | Asp  |
|     |     |     | 250 |     |     |     |     | 255 |     |     |     |     | 260 |     |      |
| TCC | GCT | CCT | GTT | GTC | CAG | AAG | TCC | TCC | ACC | AAG | CCT | GCC | GCT | CAG | CCC  | 930 |
| Ser | Ala | Pro | Val | Val | Gln | Lys | Ser | Ser | Thr | Lys | Pro | Ala | Ala | Gln | Pro  |
|     |     | 265 |     |     |     |     | 270 |     |     |     |     | 275 |     |     |      |
| GAG | CCT | ACT | AAG | CCC | GCC | GAC | AAG | CCC | CAG | ACC | GAC | AAG | CCT | GTC | GCC  | 978 |
| Glu | Pro | Thr | Lys | Pro | Ala | Asp | Lys | Pro | Gln | Thr | Asp | Lys | Pro | Val | Ala  |
|     | 280 |     |     |     |     | 285 |     |     |     |     | 290 |     |     |     |      |
| ACC | AAG | CCT | GCT | GCT | ACC | AAG | CCC | GTC | CAA | CCT | GTC | AAC | AAG | CCC | AAG  | 1026 |
| Thr | Lys | Pro | Ala | Ala | Thr | Lys | Pro | Val | Gln | Pro | Val | Asn | Lys | Pro | Lys  |
| 295 |     |     |     | 300 |     |     |     |     | 305 |     |     |     |     | 310 |      |
| ACA | ACC | CAG | AAG | GTC | CGT | GGA | ACC | AAA | ACC | CGA | GGA | AGC | TGC | CCG | GCC  | 1074 |
| Thr | Thr | Gln | Lys | Val | Arg | Gly | Thr | Lys | Thr | Arg | Gly | Ser | Cys | Pro | Ala  |
|     |     |     |     | 315 |     |     |     |     | 320 |     |     |     |     | 325 |      |
| AAG | ACT | GAC | GCT | ACC | GCC | AAG | GCC | TCC | GTT | GTC | CCT | GCT | TAT | TAC | CAG  | 1122 |
| Lys | Thr | Asp | Ala | Thr | Ala | Lys | Ala | Ser | Val | Val | Pro | Ala | Tyr | Tyr | Gln  |
|     |     |     | 330 |     |     |     |     | 335 |     |     |     |     | 340 |     |      |
| TGT | GGT | GGT | TCC | AAG | TCC | GCT | TAT | CCC | AAC | GGC | AAC | CTC | GCT | TGC | GCT  | 1170 |
| Cys | Gly | Gly | Ser | Lys | Ser | Ala | Tyr | Pro | Asn | Gly | Asn | Leu | Ala | Cys | Ala  |
|     |     | 345 |     |     |     |     | 350 |     |     |     |     | 355 |     |     |      |
| ACT | GGA | AGC | AAG | TGT | GTC | AAG | CAG | AAC | GAG | TAC | TAC | TCC | CAG | TGT | GTC  | 1218 |
| Thr | Gly | Ser | Lys | Cys | Val | Lys | Gln | Asn | Glu | Tyr | Tyr | Ser | Gln | Cys | Val  |
|     | 360 |     |     |     |     | 365 |     |     |     |     | 370 |     |     |     |      |
| CCC | AAC | TAAATGGTAG | ATCCATCGGT | TGTGGAAGAG | ACTATGCGTC | TCAGAAGGGA |  |  |  |  |  |  |  |  |  | 1274 |
| Pro | Asn |  |  |  |  |  |
| 375 |     |  |  |  |  |  |

TCCTCTCATG AGCAGGCTTG TCATTGTATA GCATGGCATC CTGGACCAAG TGTTCGACCC  1334

TTGTTGTACA TAGTATATCT TCATTGTATA TATTTAGACA CATAGATAGC CTCTTGTCAG  1394

CGACAACTGG CTACAAAAGA CTTGGCAGGC TTGTTCAATA TTGACACAGT TTCCTCCATA  1454

AAAAAAAAAA AAAAAAAA  1473

( 2 ) INFORMATION FOR SEQ ID NO:4:

( i ) SEQUENCE CHARACTERISTICS:
        ( A ) LENGTH: 376 amino acids
        ( B ) TYPE: amino acid
        ( D ) TOPOLOGY: linear (i i) MOLECULE TYPE: protein (x i) SEQUENCE DESCRIPTION: SEQ ID NO:4:

| Met 1 | Arg | Ser | Tyr | Thr 5 | Leu | Leu | Ala | Leu | Ala 10 | Gly | Pro | Leu | Ala | Val 15 | Ser |
|---|---|---|---|---|---|---|---|---|---|---|---|---|---|---|---|
| Ala | Ala | Ser | Gly 20 | Ser | Gly | His | Ser | Thr 25 | Arg | Tyr | Trp | Asp | Cys 30 | Cys | Lys |
| Pro | Ser | Cys 35 | Ser | Trp | Ser | Gly | Lys 40 | Ala | Ala | Val | Asn | Ala 45 | Pro | Ala | Leu |
| Thr | Cys 50 | Asp | Lys | Asn | Asp 55 | Asn | Pro | Ile | Ser | Asn 60 | Thr | Asn | Ala | Val | Asn |
| Gly 65 | Cys | Glu | Gly | Gly | Gly 70 | Ser | Ala | Tyr | Ala | Cys 75 | Thr | Asn | Tyr | Ser | Pro 80 |
| Trp | Ala | Val | Asn | Asp 85 | Glu | Leu | Ala | Tyr | Gly 90 | Phe | Ala | Ala | Thr | Lys 95 | Ile |
| Ser | Gly | Gly | Ser 100 | Glu | Ala | Ser | Trp | Cys 105 | Cys | Ala | Cys | Tyr | Ala 110 | Leu | Thr |
| Phe | Thr | Thr 115 | Gly | Pro | Val | Lys | Gly 120 | Lys | Lys | Met | Ile | Val 125 | Gln | Ser | Thr |
| Asn | Thr 130 | Gly | Gly | Asp | Leu | Gly 135 | Asp | Asn | His | Phe | Asp 140 | Leu | Met | Met | Pro |
| Gly 145 | Gly | Gly | Val | Gly | Ile 150 | Phe | Asp | Gly | Cys | Thr 155 | Ser | Glu | Phe | Gly | Lys 160 |
| Ala | Leu | Gly | Gly | Ala 165 | Gln | Tyr | Gly | Gly | Ile 170 | Ser | Ser | Arg | Ser | Glu 175 | Cys |
| Asp | Ser | Tyr | Pro 180 | Glu | Leu | Leu | Lys | Asp 185 | Gly | Cys | His | Trp | Arg 190 | Phe | Asp |
| Trp | Phe | Glu 195 | Asn | Ala | Asp | Asn | Pro 200 | Asp | Phe | Thr | Phe | Glu 205 | Gln | Val | Gln |
| Cys | Pro 210 | Lys | Ala | Leu | Leu | Asp 215 | Ile | Ser | Gly | Cys | Lys 220 | Arg | Asp | Asp | Asp |
| Ser 225 | Ser | Phe | Pro | Ala | Phe 230 | Lys | Val | Asp | Thr | Ser 235 | Ala | Ser | Lys | Pro | Gln 240 |
| Pro | Ser | Ser | Ser | Ala 245 | Lys | Lys | Thr | Thr | Ser 250 | Ala | Ala | Ala | Ala | Ala 255 | Gln |
| Pro | Gln | Lys | Thr 260 | Lys | Asp | Ser | Ala | Pro 265 | Val | Val | Gln | Lys | Ser 270 | Ser | Thr |
| Lys | Pro | Ala 275 | Ala | Gln | Pro | Glu | Pro 280 | Thr | Lys | Pro | Ala | Asp 285 | Lys | Pro | Gln |
| Thr | Asp 290 | Lys | Pro | Val | Ala | Thr 295 | Lys | Pro | Ala | Ala | Thr 300 | Lys | Pro | Val | Gln |
| Pro 305 | Val | Asn | Lys | Pro | Lys 310 | Thr | Thr | Gln | Lys | Val 315 | Arg | Gly | Thr | Lys | Thr 320 |
| Arg | Gly | Ser | Cys | Pro 325 | Ala | Lys | Thr | Asp | Ala 330 | Thr | Ala | Lys | Ala | Ser 335 | Val |
| Val | Pro | Ala | Tyr 340 | Tyr | Gln | Cys | Gly | Gly 345 | Ser | Lys | Ser | Ala | Tyr 350 | Pro | Asn |
| Gly | Asn | Leu 355 | Ala | Cys | Ala | Thr | Gly 360 | Ser | Lys | Cys | Val | Lys 365 | Gln | Asn | Glu |
| Tyr | Tyr 370 | Ser | Gln | Cys | Val | Pro 375 | Asn | | | | | | | | |